US00PP11432P

United States Patent [19]

Trees

[11] Patent Number: Plant 11,432

[45] Date of Patent: Jun. 27, 2000

[54] GERANIUM PLANT NAMED 'BFP-1695'

[75] Inventor: Scott C. Trees, Nipomo, Calif.

[73] Assignee: Ball Floraplant, a division of Ball Horticultural Co., West Chicago, Ill.

[21] Appl. No.: 09/114,057

[22] Filed: Jul. 10, 1998

[51] Int. Cl.[7] ..... A01H 5/00

[52] U.S. Cl. ..... Plt./329

[58] Field of Search ..... Plt./325, 329

[56] References Cited

U.S. PATENT DOCUMENTS

P.P. 9,589 6/1996 Trees ..... Plt./325

P.P. 11,075 10/1999 Hanes ..... Plt./329

*Primary Examiner*—Howard J. Locker

*Assistant Examiner*—Kent L. Bell

*Attorney, Agent, or Firm*—C. A. Whealy

[57] ABSTRACT

A new and distinct cultivar of Geranium plant named 'BFP-1695', characterized by its numerous semi-double purple-colored flowers; upright and rounded growth habit; vigorous and basal branching; and medium green leaves with a slight zonation pattern.

1 Drawing Sheet

BACKGROUND OF THE INVENTION

The present invention relates to a new and distinct cultivar of Geranium plant, botanically known as *Pelargonium×hortorum,* and hereinafter referred to by the cultivar name 'BFP-1695'.

The new Geranium is a product of a planned breeding program conducted by the Inventor in Arroyo Grande, Calif. The objective of the breeding program was to develop new cultivars with excellent basal branching, medium growth habit, numerous flowers and umbels, and interesting flower and foliage colors.

The new Geranium originated from a cross made by the Inventor of the propietary *pelargonium×hortorum* selection 6713-21 as the male, or pollen parent, with the propietary *Pelargonium×hortorum* selection 7074-21 as the female, or seed parent. The cultivar BFP-1695 was discovered and selected by the Inventor as a flowering plant within the progeny of the stated cross is a controlled environment in Arroyo Grande, Calif., on Sep. 15, 1996.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'BFP-1695'. These characteristics in combination distinguish 'BFP-1695' as a new and distinct cultivar:

1. Numerous semi-double purple-colored flowers.
2. Upright and rounded growth habit.
3. Vigorous and basal branching.
4. Medium green leaves with a slight zonation pattern.

The new Geranium can be compared to the cultivar, 'BFP-721 Bright Lilac' (disclosed in U.S. Plant Pat. No. 9,217). However, in side-by-side comparisons conducted by the Inventor in Arroyo Grande, Calif., plants of the new Geranium differ from plants of the cultivar 'BFP-721 Bright Lilac' in the following characteristics:

1. Plants of the new Geranium are more vigorous and larger than plants of the cultivar 'BFP-721 Bright Lilac'.
2. Leaves of plants of the new Geranium have a slight zonation pattern whereas leaves of plants of the cultivar 'BFP-721 Bright Lilac' do not have a discernible zonation pattern.
3. Flowers of plants of the new Geranium are larger and have more petals/petaloids than flowers of plants of the cultivar 'BFP-721 Bright Lilac'.

A detailed comparison of plants of the cultivar 'BFP-1695' and the cultivar 'BFP-721 Bright Lilac' appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in a colored reproduction of this type. The photograph comprises a top perspective view of a typical plant of 'BFP-1695'. Flower and foliage colors in the photograph may appear different from the actual colors due to light reflectance.

DETAILED BOTANICAL DESCRIPTION

The cultivar 'BFP-1695' has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a grass-covered greenhouse with day temperatures about 22° C. and night temperatures about 18° C.

In the following description, color references are made to The Royal Horticultural Society Colour Chart except where general terms of ordinary dictionary significance are used.

Botanical classification: *Pelargonium×hortorum* cultivar 'BFP-1695'.

Parentage:

*Male parent.*—Propietary *Pelargonium×hortorum* selection 6713-21.

*Female parent*.—Propietary *Pelargonium×hortorum* selection 7074-21.

Propagation:

*Type cutting*.—Terminal cuttings.

*Time to initate roots*.—About 7 days at temperatures about 18° C.

*Time to develop roots*.—About 21 days at temperatures about 18° C.

*Rooting habit*.—Fibrous and freely branching.

Plant description:

*General apperance*.—Upright and rounded growth habit, vigorous. Approximate for 10 and 12.5-cm containers. Rapid growth rate, about eight weeks are required to produced a finished 10-cm container from a rooted cutting.

*Growth and branching habit*.—Basally branching with about two lateral branches at the base.

*Plant height, base of plant to top of leaf plane*.—About 25.6 cm.

*Plant width*.—About 22.6 cm.

*Lateral branches*.—Length; About 11.3 cm. Internode length: About 1.3 cm. Color: 146D.

*Foliage description*.—Leaves simple, generally symmetrical, abundant, opposite. Length: About 6.2 cm. Width: About 8.7 cm. Shape: Reniform with rounded apex, cordate base, and crenate margin. Texture: Velvety, both surfaces pubescent. Color: Fully expanded foliage, upper surface: Center third of leaf, 137A; outer portion, darker than 137A. Fully expanded foliage, lower surface: 137C. Venation, upper surface: 146D. Venation, lower surface: 146D. Petiole: Length: About 7.2 cm. Diameter: About 2.8 mm. Color: 146D.

Flower description:

*Flower type and habit*.—Purple-colored flowers. Very freely and continuously flowering. Flowers arranged in spherical umbels arising from apical leaf axils. Umbels displayed above or beyond the foliage. Usually about six umbels per plant. Flowers semi-double and round. Umbels persistent.

*Flowering season*.—Year-round under greenhouse conditions. In the garden, flowering is continuous from spring through summer.

*Umbels*.—Number of flowers per umbel. About 16. Diameter: About 8.8 cm. Height: About 6.3 cm.

*Flowers*.—Diameter: About 5.1 cm. Depth (height): About 2 cm.

*Flower buds*.—Length: About 1.6 cm. Diameter: About 6.5 mm. Shape: Elliptic.

*Petals*.—Quantity: About six petals with usually about three petaloids, overlapping. Aspect: Flat to slightly cupped. Length: About 3.1 cm. Width: About 2.4 cm. Shape: Obovate with rounded apex and entire margin. Texture: Smooth. Color: Fully opened, upper surface: 74B to 80B with white at base giving the flower a "white-eyed" appearance. Fully opened, lower surface: 73A. Petaloids: Irregular in shape with very narrow white, 155D, base; about 1.9 cm in length and about 1.2 cm in width; between 74B and 80B in color.

*Peduncle* (*umbel stem*).—Length: About 15 cm. Strength: Strong. Angle: Mostly erect. Texture: Pubescent: Color: 146D.

*Pedicel* (*individual flower stem*).—Length; About 2.8 cm. Strength: Strong. Angle: Upright or outward. Texture: Pubescent. Color: 146A over laid with 183B becoming more red, 183B, with age.

*Reproductive organs*.—Androecium: Anther size: About 2.2 mm. Amount of pollen: Moderate. Pollen color: 34A. Gynoecium: Ovary color: Green.

Disease resistance: Under commercial conditions, resistance to pathogens has not been observed.

Seed development: Seed production has not been observed.

CHART A

| CHARACTERISTIC | 'BFP-1695' | 'BFP-721 BRIGHT LILAC' |
|---|---|---|
| VIGOR | Vigorous | Moderate |
| PLANT HEIGHT | About 25.6 cm | About 19.3 cm |
| PLANT WIDTH | About 22.6 cm | About 21.3 cm |
| LATERAL BRANCH LENGTH | About 11.3 cm | About 10.7 cm |
| LEAF LENGTH | About 6.2 cm | About 7 cm |
| LEAF WIDTH | About 8.7 cm | About 8.2 cm |
| LEAF COLOR, UPPER SURFACE | Center third of leaf, 137A; outer portion, darker than 137A | 137A, no zonation pattern |
| FLOWER DIAMETER | About 5.1 cm | About 4.6 cm |
| NUMBER OF PETALS/PETALOIDS PER FLOWER | About 11 | About 8 |
| PEDUNCLE LENGTH | About 15 cm | About 14 cm |

It is claimed:

1. A new and distinct cultivar of Geranium plant named 'BFP-1695', as illustrated and described.

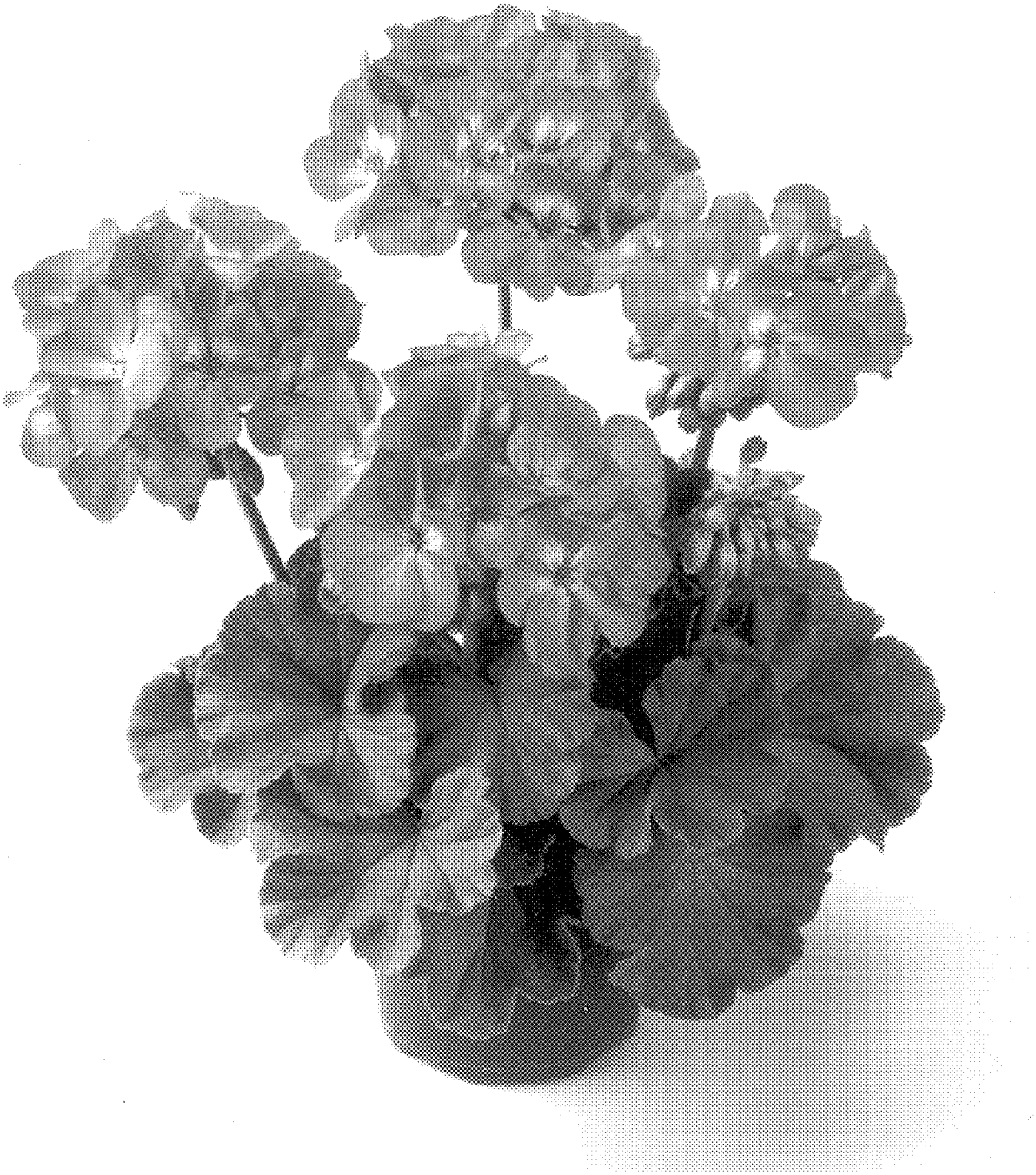

* * * * *